United States Patent [19]

Webb

[11] Patent Number: 4,621,665

[45] Date of Patent: Nov. 11, 1986

[54] METHOD OF AND APPARATUS FOR SIMULTANEOUSLY FILLING THE CUP-SHAPED CAVITIES OF A MICROBEAKER PLATE

[75] Inventor: Leslie Webb, Düren-Echtz, Fed. Rep. of Germany

[73] Assignee: Kernforschungsanlage Julich GmbH, Julich, Fed. Rep. of Germany

[21] Appl. No.: 713,437

[22] Filed: Mar. 19, 1985

[30] Foreign Application Priority Data

Mar. 22, 1984 [DE] Fed. Rep. of Germany ....... 3410508

[51] Int. Cl.$^4$ .............................................. B65B 3/04
[52] U.S. Cl. ........................................ 141/1; 141/116; 141/237; 73/863.32; 73/864.11; 422/100
[58] Field of Search ....................................... 141/1–12, 141/115–127, 234–248, 250–284, 18–31, 114, 67, 286; 73/863.32, 864.11; 422/99, 100, 101, 102, 103, 104

[56] References Cited

U.S. PATENT DOCUMENTS 3,197,082 7/1965 Palombo ............................. 141/117
3,661,189 5/1972 Bowser et al. ......................... 141/1

FOREIGN PATENT DOCUMENTS 7621180 2/1977 France .

*Primary Examiner*—Houston S. Bell, Jr.
*Attorney, Agent, or Firm*—Karl F. Ross; Herbert Dubno

[57] ABSTRACT

An apparatus for simultaneously filling a set of microcups includes a corresponding number of storage vessels having capillary outlets projecting into the microcups. The distance between the outlets and the bottom of the microcups is adjustable so that the filling quantity of the microcups can be modified depending on the requirements. For discharging fluid out of the storage vessels into the aligned microcups, diaphragms are used which are connected directly to the storage vessels or to auxiliary vessels cooperating with the storage vessels and are acted upon by a pressure plate located above the diaphragms. By pushing the pressure plate against the diaphragms, an overpressure is caused above the liquid within the storage vessel so that at first an excessive amount of liquid is discharged into the microcups. Upon release of the pressure, the diaphragms return to their initial position thus drawing in the excessive amount of liquid.

12 Claims, 8 Drawing Figures

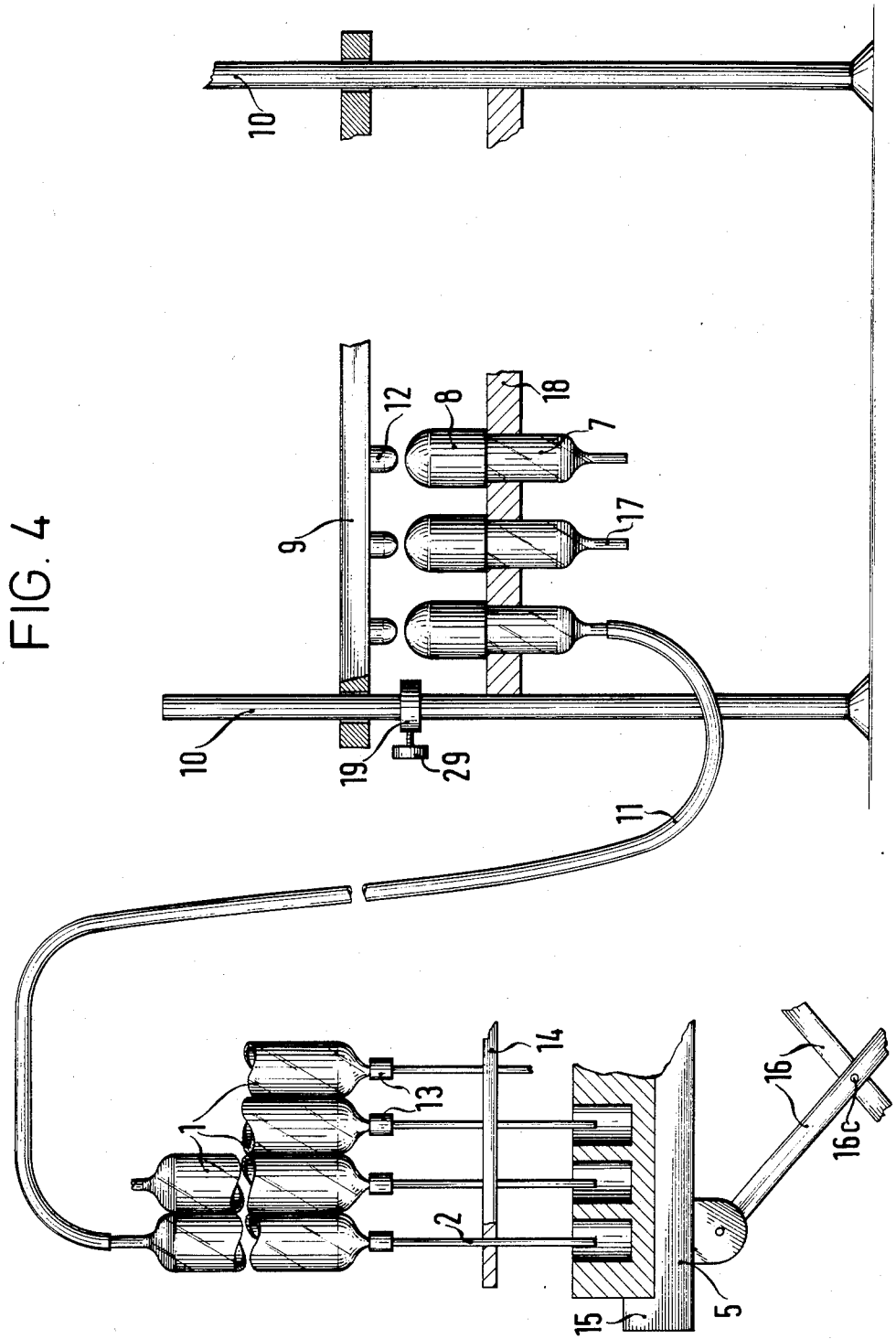

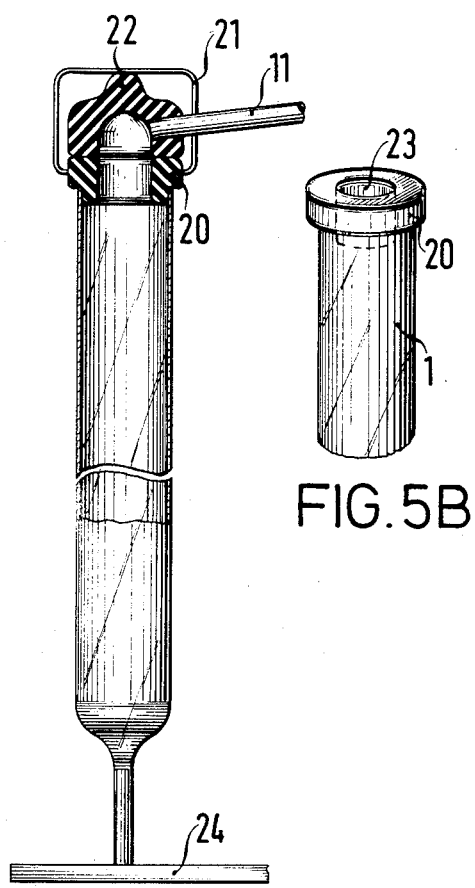
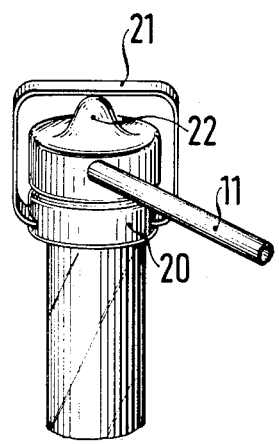
FIG. 5A
FIG. 5C
FIG. 5B

METHOD OF AND APPARATUS FOR SIMULTANEOUSLY FILLING THE CUP-SHAPED CAVITIES OF A MICROBEAKER PLATE

FIELD OF THE INVENTION

My present invention relates to a method of and to an apparatus for simultaneously filling a set of cups and, more particularly, the cup-shaped cavities or recesses of a microbeaker plate, hereinafter referred to variously as microcups or microbeakers.

BACKGROUND OF THE INVENTION

In general, in analytical systems aliquots of a reagent or medium must be prepared in micro-quantities. Biochemical procedures also use plates, hereinafter referred to as microbeaker plates, having orthogonal rows of cup-shaped cavities or recesses of limited depth and limited volumetric capacity into which it is desired to dispense small but equal quantities of a liquid. The microcups cooperate with a corresponding number of storage vessels which contain a liquid and are connected to tubes aligned with the microcups. By increasing the pressure above the liquid level within each storage vessel, the liquid is discharged from the latter into the aligned microcup.

Such an apparatus, which may be referred to as a "dispensing device" or "dispenser" is marketed by Dynatech Produkte AG, Kloten (Switzerland) under the tradename "AM 160 MIC-2000" and can be used to fill 96 microcups of a microcup or microbeaker plate, e.g. the Microtiter$^{(R)}$ plate. The dispensing device includes a test tube rack with 96 open test tubes from which transfer tubes extend to a dispensing head provided with 96 individual valves and having outlet openings opposite to the 96 microcups of the plate. The test tubes are accommodated in an enclosed space whereby the transfer tubes project through appropriate seals towards the exterior. Leading into the space is a pipe connected to a compressor and including a regulator for increasing the pressure above the test tubes.

Through controlled pressure increase, liquid can be forced out of the test tubes to the dispenser head via the transfer tubes. The valves are simultaneously opened and closed by a separate control mechanism so that a requisite liquid quantity is discharged into each of the microbeakers.

This commercial product is complicated to control and operate and is also relatively expensive.

OBJECTS OF THE INVENTION

It is thus the principal object of my invention to provide an improved filling apparatus which obviates the aforestated drawbacks.

Another object of the invention is to provide a relatively simple, inexpensive and easily controlled dispenser for simultaneously delivering predetermined quantities of liquid to the cup-shaped microcavities of a microbeaker plate with a satisfactory level of precision.

SUMMARY OF THE INVENTION

I realize this object, according to the present invention, by controlling the distance between the outlets of the respective delivery tubes communicating with the respective storage vessels and the bottoms of the respective microcups by means of an adjusting mechanism and by providing an airtight elastic diaphragm cooperating with each storage vessel as the means for increasing the pressure above the fluid level within each storage vessel so that depending on the distance between the respective outlets and the bottom of the microcups, the latter are filled with a predetermined amount of fluid.

The diaphragms can be either connected in an airtight manner directly onto the storage vessels or can be connected to auxiliary vessels which are then operatively connected with the storage vessels via respective tubes. Above the plurality of diaphragms, a pressure plate is arranged which is lowered towards the diaphragms to press the latter into the interior of the associated vessel (either storage vessel or auxiliary vessel) so that the pressure above the fluid level within the storage vessels is increased and fluid is discharged.

According to the teachings of my invention, the microcups are first filled with an excess of liquid once the diaphragms are depressed by the pressure plate; however, when the pressure on the diaphragms is released, the latter are returned into their initial positions due to their elasticity so that the excess of liquid is drawn back into the storage vessel until the discharge tubes of the storage vessels are no longer immersed in the liquid in the microcups so that no further liquid is returned into the storage vessels. It is obvious that the quantity of liquid which will be left in the microcups depends on the distance between the outlet end of the discharge tubes and the bottom of the microcups and is thus adjustable with precision by modifying the distance between the bottom of each cup and the tip of the delivery tube cooperating therewith.

It is thus a prerequisite that the microplate lie with precision in a horizontal position to obtain the same liquid quantity in each microcup. In addition, the uniformity of the microcups or cavities and their bottom depth as well as a horizontal alignment of the outlets of the storage vessels must be ensured to secure an equal degree of filling of all the microcups. I may note, however, that microcup plates with practically uniform dimensions are available (also because of the usual auxiliary devices) so that the apparatus according to my invention provides a uniform filling accuracy with a tolerance of at the most ±10%.

According to a further feature of my invention, the diaphragms are constituted by rubber caps which preferably are of hemispherical shape and of such elastic material that they can easily be pressed to reduce the required force and automatically return in their initial position after release of pressure via the pressure plate despite the additional load of the liquid column within the storage vessels.

For adjusting the distance between the storage vessels and the microcups, the latter i.e. the microcup plate which contains the microcups is placed on a table which can be elevated or lowered in a vertical direction by a lever assembly attached thereto. The lever assembly includes at each side of the table two scissor-like arms which cooperate with an adjusting lever projecting towards the outside to allow adjustment of the table from outside. This mechanism ensures that in all positions the table will remain horizontal, i.e. will always move parallel to itself. Alternatively there may be e.g. rails especially acting together with a hydraulic mechanism.

In order to accommodate a large amount of liquid within the storage vessels despite the close arrangement of the outlets above the microcups, the outlets of the storage vessels are provided as capillary tubes via tube couplings and the storage vessels are arranged in a spread formation. To obtain the spread arrangement, tubular storage vessels with corresponding cross section are extended over a certain length by narrower (flexible) tubes which allow a transition of the close arrangement of the capillary tubes to the spreaded arrangement of the storage vessels.

It is, however, also possible to provide conical storage vessels to obtain a large storage volume for the fluid.

In order to allow easy filling of liquid into the storage vessels, the latter are provided at their end section remote from the capillary tubes with a flange portion which includes an opening through which the fluid can be introduced. Once sufficient liquid is introduced, the storage vessels are sealed off by a locking cap which is pressed to the flange by means of a clamp strap. For the filling operation the outlets of the capillary tubes must be closed which could be done by pressing a sealing plate against them.

The apparatus according to the invention is simple and very economical concerning its production as well as its maintenance.

BRIEF DESCRIPTION OF THE DRAWING

The above and other objects, features and advantages of my present invention will become more readily apparent from the following description, reference being made to the accompanying drawing, in which:

FIG. 4 is a more detailed illustration of the filling apparatus according to FIG. 1;

FIGS. 5a, 5c illustrate one storage vessel with its upper portion sealed by a locking device; and FIG. 5b is a perspective view of the upper portion of one storage vessel without the locking device.

SPECIFIC DESCRIPTION

Figure 1:
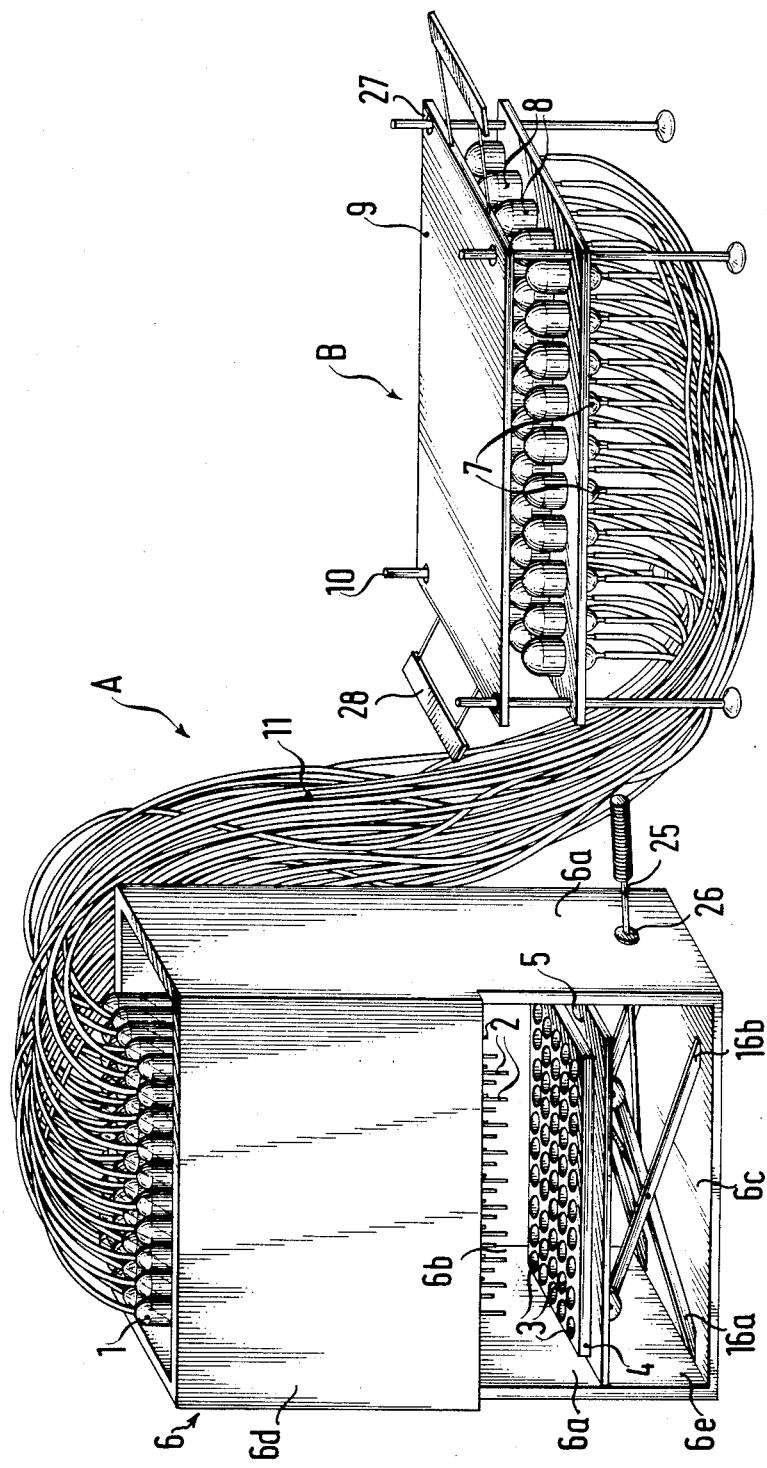
FIG. 1 is a schematic illustration in perspective view of a preferred embodiment of a filling apparatus according to the invention.

In the drawing, there can be seen a filling apparatus essentially consisting of two portions A, B communicating with each other. The portion A includes a casing 6 having two opposing side walls 6a, a rear wall 6b, a bottom wall 6c and a front wall 6d which is of reduced size so that an access opening 6e is defined to allow a set of microcups or cuvettes 3 which are to be filled with a fluid to be positioned within the casing 6 as will be described hereinbelow.

The microcups 3 are formed as cavities in a plate 4 which is placed on a table 5. The table 5 is vertically adjustable, preferably along a guide rail arrangement (not shown) in the casing 6, by a lever assembly 16 which includes two arms 16a, 16b provided in a scissor-like manner along each side of the table 5. The arms 16a, 16b are connected to each other via a joint 16c and are hinged with their upper extremities to the table 5 as shown in FIG. 4 while their lower extremities are supported on the bottom 6c. Cooperating with the arms 16a, 16b is an adjusting lever 25 which extends through an opening 26 in one of the side walls 6a to project towards the outside so that e.g. by turning lever 25 in either direction, the arms 16a, 16b are moved towards or away from each other thereby correspondingly controlling the height of the table 5. A laboratory scissor or other jack can be used for this purpose, the key being that the device can raise and lower the plate with precision while keeping it parallel to itself and horizontal.

Figure 2:
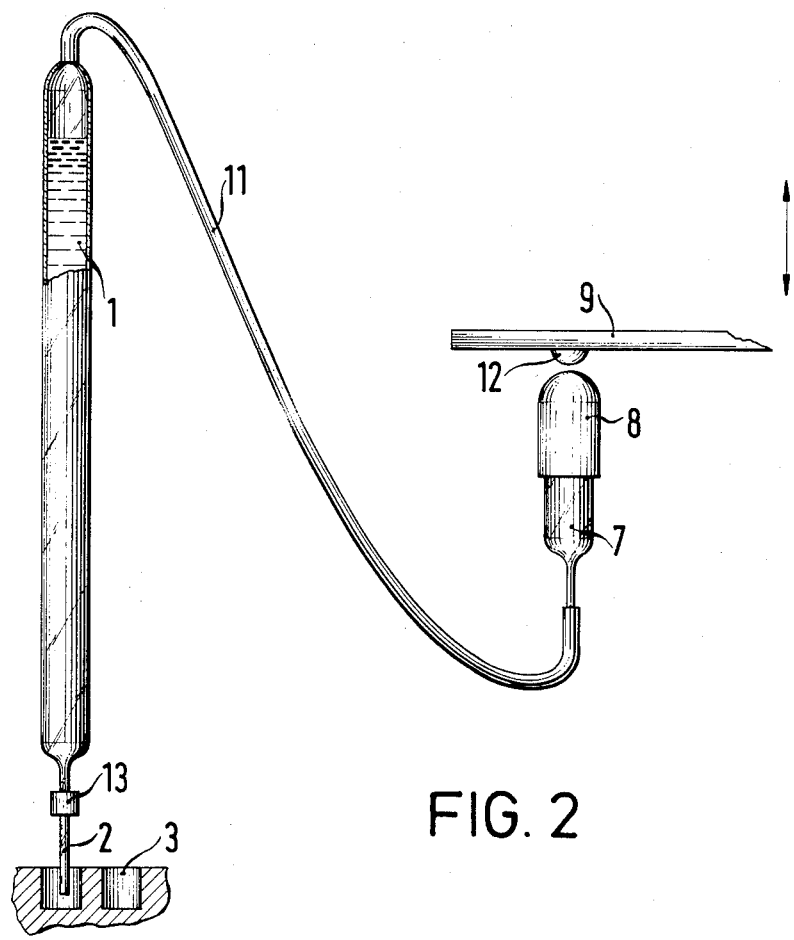
FIG. 2 is a schematic illustration of one storage vessel of the filling apparatus in FIG. 1 and its connection with an associated auxiliary vessel.

Arranged above the set of microcups 3 is a number of storage vessels 1 which are filled with fluid as indicated by dots in FIG. 2 and retained within the casing 6 in any suitable manner. Each of the storage vessels 1 is of an elongated shape and has one end section which faces the microcups 3 being tapered to form a capillary tube 2. In a preferred embodiment, however, the capillary tubes 2 are separate parts which are connected to the end section of the vessels 1 via respective tube couplings 13 and are mounted in a common rack 14 engaging in a guide rail (not shown) of the casing 6. Each of the capillary tubes 2 is made of stainless steel.

In order to obtain an exact alignment between opposing vessels 1 and microcups 3, the table 5 is provided with stop members 15 against which the plate 4 abuts when positioned on the table 5.

The other end section of each vessel 1 is also tapered as is especially shown in FIG. 4.

The portion B of the filling apparatus is arranged separately from the portion A and includes a set of auxiliary vessels 7 which are individually arranged in a rack 18. As is illustrated in FIG. 1, the rack 18 is fixed with its ends to respective upright posts 10. Each vessel 7 is provided with a capillary end 17 over which one end of a tube 11 e.g. a silicone tube, is slipped over whose other end is connected to the associated one of the storage vessels 1. At its end remote to the tube 11, each vessel 7 is provided with a diaphragm 8 e.g. a rubber cap which is essentially of semispherical shape and of elastic material. Each diaphragm 8 cooperates with a pressure plate 9 arranged at a distance to the set of vessels 7. The pressure plate 9 is provided with a hole 27 at each corner thereof through which the posts 10 project so that the plate 9 is movably guided along the posts 10 in a vertical direction via hand grips 28 which are provided at opposing sides of the pressure plate 9.

As can be seen from FIG. 4, the pressure plate 9 is provided with a plurality of projections 12 at its surface opposing the vessels 7. The projections 12 are arranged in such manner that the rubber cap 8 of each vessel 7 is aligned with one projection of the plate 9. For limiting the downward movement of the pressure plate 9, stop members 19 are clamped to the posts 10. The position of each stop member 19 along the posts 10 is adjustable by means of a screw 29.

I may note, however, that it is certainly within the scope of the present invention to provide the diaphragms 8 directly on the storage vessels and to arrange the pressure plate 9 above the diaphragms 8 to obtain the pressure increase above the liquid within the vessels 1. In this case, the auxiliary vessels 7 and the tubes 11 can be omitted.

After having described the individual parts of the filling apparatus, I will now explain in detail the mode of operation.

Figure 3A:
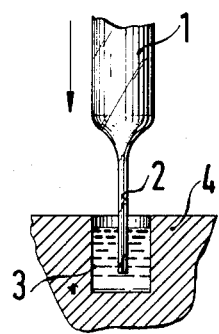
FIGS. 3a, 3b illustrate two stages of the filling process according to the invention.
Figure 3B:
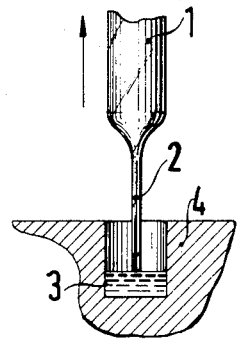

Once the plate 4 of microcups 3 is placed on the table 5 and the latter is moved into the correct position (by lever assembly 16) so that each of the capillary tubes 2 projects into an aligned microcup 3 (FIG. 3a) by an amount depending on the predetermined filling level, the pressure plate 9 is pushed downwardly—usually manually—by means of the grips 28 against the rubber caps 8 until the latter are pressed by the projections 12 into the vessels 7. Consequently, an overpressure is generated above the level of fluid within the vessel 1 which overpressure causes fluid to be discharged in an excessive amount out of the capillary tubes 2 into the aligned microcups 3 (FIG. 3a).

When the pressure on the plate 9 is released, the rubber caps 8 will return into their initial position due to their elasticity thereby drawing in fluid out of the microcups 3 into the respective vessels 1—because of the under pressure above the fluid—until the outlet of each capillary tube does not immerse into the fluid anymore and the requested quantity of fluid is provided into the microcups 3.

Therefore, by adjusting the distance between the outlet of the capillary tube and the bottom of each microcup 3, the filling degree of each microcup 3 can be determined. As mentioned, the adjustment is primarily provided by adjusting the height of the table 5.

Turning now to FIGS. 5a, 5b and 5c, it can be seen that the end section of each vessel connected to one tube 11 is not tapered as has been illustrated in FIG. 4 but is flat and provided with a jacket or flange 20 which has a central opening 23 (FIG. 5b). Cooperating with the flange 20 is a locking cap 22 which is pressed against the flange 20, if necessary via an intermediate silicone sealing ring (not shown), by a clamp strap or bail 21. Alternatively the upper open end of the storage vessel could simply be closed by a stopper through which a tube passes.

The tube 11 extending from an associated vessel 7 is connected to the locking cap 22. This embodiment considerably facilitates the filling of the vessels 1 as the fluid can simply be introduced through the opening 23 by removing the locking cap 22 and using a finely drawn pipette (enzyme pipette). During the filling step of each vessel 1, the lower ends of the capillary tubes 2 are sealed off by pressing the latter against a sealing plate 24, as is illustrated in FIG. 5a.

The storage capacity of each vessel 1 allows a filling of approximately 120 sets of microcups 3. If necessary, sterile filters (not shown) can be provided between the portions A and B e.g. within the tubes 11. Since portion A does not include any movable parts, it can easily be sterilized within an autoclave.

I claim:

1. A method of simultaneously filling a set of cups with a liquid, comprising the steps of:
   (a) placing above the cups a plurality of storage vessels which contain the liquid;
   (b) aligning an outlet opening of each storage vessel with a respective one of the cups by adjusting the distance therebetween;
   (c) increasing the pressure within each storage vessel by pressing against a respective elastic diaphragm which is individual to and operatively connected with the respective storage vessel so as to force liquid into each of the cups in excess; and
   (d) releasing the pressure on the diaphragms so that the diaphragms return into their initial shape thereby drawing in excess liquid out of the cups back into the storage vessels for providing a predetermined liquid quantity within each of the cups.

2. A method as defined in claim 1 wherein step (c) includes pushing a pressure plate against the diaphragms to deform the latter.

3. A method as defined in claim 2 wherein step (d) includes bringing the pressure plate out of contact with the diaphragms.

4. An apparatus for filling a set of cups with a liquid, comprising:
   a microbeaker plate formed with a multiplicity of identical solid-wall cavities having respective bottoms at a fixed distance above a bottom surface of said plate and each constituting one of said cups;
   a respective vertically elongated storage vessel individual to each cavity and disposed above each of said cavities, said storage vessels each being formed with a large cross section upper portion and a downwardly open capillary tube extending downwardly from said upper portion into the respective cavity and containing said liquid;
   housing means for supporting all of said storage vessels so that bottom ends of the respective capillary tubes terminate in a common horizontal plane;
   a vertically adjustable support for said plate disposed below said capillary tubes for positioning said bottoms of all of said cavities at a given distance below the bottom ends of said capillary tubes;
   a respective pressure member assigned to each of said storage vessels and disposed in a common array, said pressure members being formed with respective diaphragms mechanically displaceable to press fluid from said pressure members, each of said pressure members being connected with an upper portion of a respective one of said storage vessels for driving liquid out of said storage vessels into said cavities upon the displacement of fluid from the respective pressure member and permitting retraction of liquid through said capillaries upon relief of mechanical force on said diaphragms; and
   pressure means for mechanically displacing said diaphragms of said array to deliver liquid from said storage vessels to said cavities and thereafter relieving force on said diaphragms to permit liquid above the bottom ends of said capillaries in said cavities to be drawn back into said capillaries, thereby leaving fixed amounts of said liquid in all of said cavities.

5. The apparatus defined in claim 4 wherein each of said diaphragms is a rubber cap.

6. The apparatus defined in claim 4 wherein said pressure means includes a pressure plate movable relative to said array and against said diaphragms.

7. The apparatus defined in claim 6 wherein each of said pressure members is a respective pressure vessel and said array of pressure vessels is spaced from said housing means, said pressure vessels each communicating with a respective one of said storage vessels by a respective flexible tube.

8. The apparatus defined in claim 6 wherein said plate has a surface facing said diaphragms, provided with a plurality of retractions each in alignment with and engageable with a respective one of said diaphragms.

9. The apparatus defined in claim 4 wherein said capillary tubes are separate from said storage vessels, further comprising tube couplings for connecting each of said capillary tubes with a respective one of said storage vessels.

10. The apparatus defined in claim 4, further comprising a locking cap removably affixed to an upper end of each of said storage vessels.

11. The apparatus defined in claim 4 wherein said vertically adjustable support includes a table positioned below said bottom ends of said capillary tubes for supporting said plate, said table being provided with stop members for accurately aligning said cavities with respect to said capillary tubes and a lever assembly cooperating with said table for moving said table in a vertical direction to control said distance.

12. The apparatus defined in claim 11 wherein said lever assembly includes two arms connected to said table and forming a scissor linkage at each side below said table, and an adjusting lever cooperating with said arms for shifting said table in a vertical direction, said table being disposed within said housing means.

* * * * *